United States Patent [19]

Schmidt

[11] Patent Number: 4,532,133
[45] Date of Patent: Jul. 30, 1985

[54] LOW TEMPERATURE STABLE, EMULSIFIABLE VITAMIN A CONCENTRATES

[75] Inventor: Douglass N. Schmidt, Grosse Ile, Mich.

[73] Assignee: BASF Wyandotte Corporation, Wyandotte, Mich.

[21] Appl. No.: 497,673

[22] Filed: May 24, 1983

[51] Int. Cl.³ .................... A61K 31/00; A61K 47/00; A61K 31/07
[52] U.S. Cl. ...................................... 514/725; 514/971
[58] Field of Search ................................ 424/173, 344

[56] References Cited

U.S. PATENT DOCUMENTS 3,639,587  2/1972  Ames .................................... 424/237
3,708,583  1/1973  Winstrom et al. ................... 424/173
4,022,913  5/1977  Newmark ............................ 424/344

OTHER PUBLICATIONS

Chem. Abst. 80, 100220(s) (1974)—Igimi et al.
Chem. Abst. 83, 113,655(z) (1975)—Yoneya et al.

Primary Examiner—Douglas W. Robinson
Attorney, Agent, or Firm—David L. Hedden; Joseph D. Michaels

[57] ABSTRACT

Vitamin A palmitate compositions stable against crystallization at low temperatures are prepared by blending therewith a monoterpene such as dl-limonene. Vitamin A active concentrates prepared utilizing low temperature stabilized vitamin A palmitate are prepared by blending therewith an acceptable feed or food grade emulsifier.

3 Claims, No Drawings

LOW TEMPERATURE STABLE, EMULSIFIABLE VITAMIN A CONCENTRATES

BACKGROUND OF THE INVENTION

1. Field of the Invention

This invention relates to vitamin A palmitate compositions stabilized against crystallization at low temperatures and to emulsifiable concentrates thereof.

2. Description of the Prior Art

Vitamins have been used for many years as additives for animal feed to increase the rate of weight gain and to improve resistance to disease and overall performance of the animal. Because vitamins are used in very small amounts, additives in the form of vitamin concentrates and premixes are generally used to fortify the animal feed. Generally, the vitamins are added to the animal feed in the form of emulsifiable or solubilized solutions or dispersions of the vitamins. The fat-soluble vitamins must be emulsified or solubilized prior to introduction into the animal feed to prevent layering and segregation of the vitamins in the feed. Additionally, the vitamin additives should be pourable at temperatures below about 0° C. in order that they may be useful in winter feeding programs in the northern and western states.

The fat-soluble vitamins, particularly vitamin A, in addition to having to be dispersed or emulsified prior to addition to feed, have the disadvantage in that they are characterized by having poor chemical stability. Their potency is lost upon exposure to air oxidation and/or exposure to water in the preparation of emulsions prior to addition to animal feed. It has, therefore, become the practice to provide non-aqueous, emulsifiable concentrates of vitamins, particularly vitamin A and other fat-soluble vitamins. When these concentrates contain animal feed and/or food additive-acceptable emulsifiers, the desired emulsion or dispersion can be prepared at the feed site. feed. Heretofore, the problem of providing an emulsifiable concentrate containing vitamin A which is stable at temperatures below the solidification temperature of vitamin A acetate or vitamin A palmitate in the pure state, has been solved by the use of various stabilization additives. These additives have included oxyalkylene compounds and short chain alkyl alcohols.

In U.S. Pat. No. 4,022,913, there are disclosed vitamin A acetate compositions stabilized against the formation of crystals at low temperatures (about 5° C.) by the inclusion of vitamin A palmitate. This was unexpected in view of the fact that both vitamin A acetate and vitamin A palmitate in the pure state are solids at such temperatures.

In U.S. Pat. No. 3,639,587, there are disclosed non-aqueous vitamin-active preparations having crystallization temperatures below about 4° C. which can include vitamin A. The compositions are stabilized against crystallization by the inclusion of a polyoxyethylene material and a viscosity reducing agent such as an ester of a lower alkyl alcohol.

In U.S. Pat. No. 3,708,583, there is disclosed a stabilized vitamin additive containing a mixture of vitamin A acetate and vitamin A palmitate in combination with a lower alkyl alcohol and a nonionic emulsifier.

SUMMARY OF THE INVENTION

The stable, vitamin A active concentrates of the invention can comprise, besides vitamin A palmitate, other fat-soluble vitamins in combination with a monoterpene such as dl-, l-, and d-limonene. In order to prepare vitamin A active concentrates containing the stabilized vitamin A palmitate of the invention, it is optionally desirable to include in a blend therewith a short chain alkyl alcohol. A suitable emulsifier system must be present which is acceptable in animal feed and/or classed as a food grade additive for human consumption. Because of the low temperature stabilizing effect of the monoterpene, the vitamin A palmitate is stable against crystallization at low temperatures such as a range of about −4° C. to about 0° C., which is below the temperature at which vitamin A palmitate solidifies in the pure state.

DETAILED DESCRIPTION OF THE INVENTION

Vitamin A palmitate can be stabilized against crystallization at temperatures below its solidification temperature of about 24° to 28° C. in the pure state by the incorporation of a monoterpene such as dl-limonene (dipentene). Vitamin A occurs naturally both as the alcohol and as the palmitate ester of that alcohol. The commercial forms of vitamin A are the palmitate, the propionate, and the acetate esters of the vitamin. These esters are generally synthesized from materials other than naturally occurring vitamin A.

In addition to the required use of vitamin A palmitate in the stabilized, emulsifiable, non-aqueous liquid concentrate compositions of the invention, these compositions can contain major or minor amounts of other fat-soluble vitamins such as vitamin E, vitamin D, and vitamin K. While the vitamin A palmitate compositions of the invention can contain vitamin A palmitate as the sole source of vitamin A, blends of a major proportion of vitamin A palmitate with a minor proportion of other sources of vitamin A, such as vitamin A acetate, vitamin A alcohol, and vitamin A propionate are useful. The proportion of the source of vitamin A in the concentrates of the invention is by weight about 20 percent to about 40 percent, preferably about 22 percent to about 35 percent, and most preferably about 24 percent to about 30 percent, all based upon the weight of said concentrate.

As the stabilizer against crystallization for the vitamin A palmitate-containing compositions of the invention, it has been found that a monoterpene is effective generally in amounts of about 5 percent to about 15 percent by weight based upon the weight of the vitamin A palmitate-containing concentrate. Preferably, about 6 percent to about 10 percent by weight and most preferably about 7 percent to about 9 percent by weight of a monoterpene is useful, all based upon the weight of said concentrate.

The useful monoterpenes are customarily considered as derivatives of isoprene. The carbon skeletons of the monoterpenes are made up of two isoprene units connected head to tail. The name "terpene" is not limited to unsaturated hydrocarbons. Terpenes can also include not only isoprene oligomers but also their oxygenated derivatives such as terpene alcohols, ketones, aldehydes, acids, etc. For the purposes of this invention, a monoterpene is defined as limited to the unsaturated hydrocarbon members of the terpene series. Nearly all technologically important monoterpenes were of biochemical origin until recently. The monoterpene crystallization inhibitors are, of course, related to vitamin A which is a diterpene and to carotene which is a tetraterpene. Dl-, d-, and l-limonene are useful monoterpene crystallization inhibitors. The preferred dl-limonene (dipentene) is a racemic mixture of the dextro- and levorotatory isomers in which half of the optically active isomers are capable of rotating plane polarized light to the right or the left. The opposite rotations cancel each other in the racemized mixture referred to as dl-limonene or dipentene.

Lower alkyl alcohols having from 2 to 3 carbon atoms are useful in the preparation of the vitamin A active stabilized concentrates of the invention as diluents or solvents for the vitamin A palmitate. Useful alcohols are selected from the group consisting of ethyl alcohol, n-propyl alcohol and mixtures thereof. These alcohols are useful generally in the proportions by weight of about 3 to about 15 percent, based upon the weight of the vitamin A palmitate-containing concentrate, preferably about 4 to about 10 percent, and most preferably about 4 to about 6 percent by weight, all based upon the weight of said concentrate. These alcohols are miscible in both water and many oils and can, therefore, be utilized as solvents for most of the forms of the fat-soluble vitamins. These alcohols also serve to control the viscosity of the vitamin A palmitate-containing concentrates and act as secondary emulsifiers. Additionally, the alcohols can act as freeze depressants.

The emulsifier system utilized in the emulsifiable vitamin A palmitate-containing concentrates of the invention can be selected from the various nonionic emulsifiers. The emulsifiers used must be acceptable as additives in food or in animal feeds and have no deleterious effect upon the vitamin A palmitate or other fat soluble vitamin used therewith or upon the effectiveness of the lower alkyl alcohol utilized as a solvent or diluent.

Generally, the emulsifier system should have a hydrophilic-lipophilic balance (HLB) suitable to provide self-emulsification properties to the vitamin A palmitate-containing concentrate. The HLB of the emulsifier system should be about 3 to about 17, preferably about 5 to about 14, and most preferably about 10 to about 14. Generally, most nonionic emulsifiers or mixtures of nonionic emulsifiers will meet these criteria. The proportion by weight of emulsifier utilized in the emulsifiable vitamin A palmitate-containing concentrates of the invention is generally about 25 percent to about 60 percent, preferably about 35 percent to about 55 percent, and most preferably about 40 percent to about 50 percent, all based upon the weight of said emulsifiable concentrates. A practical emulsifier system must have an adequate balance between the oil emulsified and the water in which the emulsification takes place. The required HLB will decrease as the oil phase becomes less hydrophilic, for instance, as the carbon number of a straight chain alcohol increases. Generally, an HLB range will provide satisfactory results, however, this range will narrow as the oil and water phases become more widely separated in properties.

The following specific examples of animal feed or food grade emulsifiers are useful in the emulsifiable concentrates of the invention: sorbitan monostearate, polyoxyethylene glycol monooleate, polyoxyethylene glycol dioleate, polyethylene glycol mono- and dioleate, mono- and diglycerides of animal fats, monoglycerides of coconut oil, monoglycerides of peanut oil, and propylene glycol.

Because of the sensitivity to chemical deterioration of vitamin A palmitate, other forms of vitamin A, and other fat-soluble vitamins, it is helpful to incorporate an antioxidant in the vitamin A palmitate-containing concentrates of the invention. One of the useful antioxidants known in the art which can be used herein is termed ethoxyquin which is otherwise known as 6-ethoxy-1,2-dihydro-2,2,4-trimethylquinolin. The use of such an antioxidant lengthens the shelf life and minimizes the chemical deterioration and degradation of such fat-soluble vitamins as vitamin A palmitate. It is believed that the ethoxyquin is preferentially oxidized in solution and thereby protects the fat-soluble vitamins from chemical deterioration and degradation.

Yeast and mold inhibitors and other preservatives optionally can also be added to the vitamin A palmitate-containing concentrates of this invention. Such compounds as butylated hydroxy toluene, butylated hydroxy amine, sorbic acid and sodium propionate are useful yeast and mold inhibitors and preservatives. Various flavoring agents other than limonene can be added to the vitamin A palmitate concentrates to improve the flavor qualities.

The proportions of antioxidants, yeast, and mold inhibitors, preservatives, and flavoring agents which are useful can be determined by one skilled in the art without extensive testing. Generally, amounts less than about 10 to about 20 percent by weight based upon the weight of the concentrates of the invention can be used. The proportion of the antioxidant ethoxyquin utilized to minimize chemical deterioration of the fat-soluble vitamins is limited by the present requirements of the Food and Drug Administration to 0.015 percent by weight of the finished feed product.

The vitamin A palmitate-containing concentrates of the invention are utilized in animal feed in amounts ranging from about 0.01 pound to about 0.5 pound per ton of animal feed. Preferably an animal feed composition is attained by the use of the concentrates of the invention which contain about 100,000 to about 400,000 international units of vitamin A palmitate per gram of concentrate. Where other fat-soluble vitamins are utilized in conjunction with the vitamin A palmitate in the concentrates of the invention, proportions of about 100 to about 100,000 international units of vitamin $D_2$, 100 to about 100,000 international units of vitamin $D_3$ and about 0.1 to about 100 international units of vitamin E are provided per gram of concentrate.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

A vitamin A palmitate concentrate was prepared by blending vitamin A palmitate (1.6 million international units per gram) 26.7 percent by weight, polysorbate 80 (POE(20) sorbitan monooleate), 10 percent by weight, polyethylene glycol 400 monooleate, 35.3 percent by weight, limonene (stabilized with 0.5 percent by weight of butylated hydroxy anisol) 10 parts by weight, n-propanol, 12 percent by weight, and ethoxyquin, 6 percent by weight. The concentrate was aged at a temperature of $-4°$ C. for a period of two weeks to evaluate the tendency of the vitamin A palmitate to crystallize. Gross visual observation after a period of two weeks at $-4°$ C. failed to reveal any change in clarity of the concentrate. Upon microscopic observation, it was noted that tiny crystals had formed in the concentrate but not to such an extent that the clarity of the concentrate was effected. Further observation of the concentrates stored at a temperature of −4° C. for a period of up to a year failed to reveal any further crystal growth or change in clarity of the concentrate.

EXAMPLE 2

A vitamin A palmitate concentrate was prepared by blending together the following ingredients: vitamin A palmitate (1.4 million international units per gram) 29 percent by weight, polysorbate 80, 16 percent by weight, polyethylene glycol 400 monooleate, 30 percent by weight, limonene (stabilized with 0.5 percent by weight of butylated hydroxy anisol) 9 percent by weight, propylene glycol diester of coconut fatty acids, 5 percent by weight, n-propanol, 5 percent by weight, and ethoxyquin, 6 percent by weight. Similar testing at −4° C. as described in Example 1 produced similar results.

EXAMPLE 3

A vitamin A palmitate/vitamin E acetate concentrate was prepared by blending together the following ingredients: vitamin A palmitate of Example 1, 26.7 percent by weight, vitamin E acetate (2.5 million international units), 10 percent by weight, polysorbate 60 (POE (20) sorbitan monostearate), 15 percent by weight, polyethylene glycol 400 monooleate, 30.3 percent by weight, limonene (stabilized with 0.5 percent butylated hydroxy anisol) 7 percent by weight, n-propanol 5 percent by weight, and ethoxyquin, 6 percent by weight. Evaluation for low temperature stability in accordance with the procedure outlined in Example 1 provided similar results.

EXAMPLE 4

Example 3 is repeated substituting vitamin A acetate for vitamin E acetate. Similar stability at low temperature is obtained.

EXAMPLES 5 AND 6

Example 4 is repeated substituting vitamin A alcohol or vitamin A propionate for the vitamin A acetate of Example 4. Similar stability at low temperatures is obtained.

While this invention has been described with reference to certain specific embodiments, it will be recognized by those skilled in the art that many variations are possible without departing from the scope and spirit of the invention and it will be understood that it is intended to cover all changes and modifications of the invention disclosed herein for the purposes of illustration which do not constitute departures from the spirit and scope of the invention.

The embodiments of the invention in which an exclusive privilege or property is claimed are defined as follows:

1. A stabilized, emulsifiable, non-aqueous Vitamin A active liquid concentrate comprising:
    (a) from about 20 percent by weight to about 40 percent by weight of Vitamin A palmitate as the sole or major source of Vitamin A,
    (b) from about 25 percent by weight to about 60 percent by weight of an animal feed or food grade acceptable emulsifier system,
    (c) from about 5 percent by weight to about 15 percent by weight of a crystallization inhibitor comprising a monoterpene, and
    (d) a lower alkyl alcohol in an amount of 0 percent by weight to about 15 percent by weight, said weight being based upon the total weight of the concentrate.

2. The stabilized vitamin A concentrate of claim 1 comprising a source of Vitamin A consisting of vitamin A palmitate or a major proportion of vitamin A palmitate and a minor proportion of vitamin A acetate, vitamin A alcohol, vitamin A propionate, or mixtures thereof and wherein said monoterpene is selected from the group consisting of dl-limonene, d-, and l-limonene.

3. The concentrate of claim 2 wherein said alkyl alcohol is selected from the group consisting of ethyl alcohol, n-propyl alcohol, and mixtures thereof.

* * * * *